(12) United States Patent
Kariya et al.

(10) Patent No.: US 9,616,356 B2
(45) Date of Patent: Apr. 11, 2017

(54) BLOWOUT

(71) Applicants: LUPINUS CO., LTD., Miyoshi-shi, Hiroshima (JP); FUKIMODO SHINOSATO CO., LTD., Awaji-shi, Hyogo (JP); Akemi Kariya, Mino-shi, Osaka (JP)

(72) Inventors: Akemi Kariya, Mino (JP); Hirokazu Yamamoto, Miyoshi (JP); Yoshio Fujimura, Awaji (JP); Yoshikatsu Kimura, Hiroshima (JP)

(73) Assignees: LUPINUS CO., LTD., Hiroshima (JP); FUKIMODOSHINOSATO CO., LTD., Hyogo (JP); Akemi Kariya, Osaka (JP)

( * ) Notice: Subject to any disclaimer, the term of this patent is extended or adjusted under 35 U.S.C. 154(b) by 0 days.

(21) Appl. No.: 14/772,763

(22) PCT Filed: Oct. 20, 2014

(86) PCT No.: PCT/JP2014/077778
§ 371 (c)(1),
(2) Date: Sep. 3, 2015

(87) PCT Pub. No.: WO2016/035220
PCT Pub. Date: Mar. 10, 2016

(65) Prior Publication Data
US 2016/0296852 A1 Oct. 13, 2016

(30) Foreign Application Priority Data
Sep. 3, 2014 (JP) ................... 2014-178704

(51) Int. Cl.
A63H 33/40 (2006.01)
A63H 37/00 (2006.01)
(Continued)

(52) U.S. Cl.
CPC ............ *A63H 33/40* (2013.01); *A61M 16/00* (2013.01); *A63B 23/18* (2013.01); *A63H 37/00* (2013.01)

(58) Field of Classification Search
CPC ....... A63H 33/40; A63H 37/00; A61M 16/00; A63B 23/18
(Continued)

(56) References Cited

U.S. PATENT DOCUMENTS 530,909 A * 12/1894 Stone ................ G10K 5/00
116/39
1,691,669 A * 11/1928 Ostendorf .............. G10D 9/026
84/399

(Continued)

FOREIGN PATENT DOCUMENTS

CN 203447775 U 2/2014
TW M337383 U 8/2008

*Primary Examiner* — Vishu Mendiratta
(74) *Attorney, Agent, or Firm* — Arent Fox LLP

(57) ABSTRACT

A blowout in which the required exhaling force of for stretching thereof may be precisely set to a suitable level. The blowout may include: a stretchable body having a generally tubular shape; a wire body having elasticity and arranged along the longitudinal direction of the stretchable body; and a mouthpiece connected to an end of the stretchable body. In use, the mouthpiece may be held in the mouth such that air is blown therethrough, whereby the stretchable body is stretched. The stretchable body remains curled into a spiral shape by the wire body when air is not blown thereinto. The elastic force of the wire body may be set to a predetermined value, the mouthpiece may include an air regulator for regulating the quantity of airflow, and the stretchable body may not stretch unless the force of air blown is equal to or more than a predetermined value.

9 Claims, 3 Drawing Sheets

(51) Int. Cl.
*A61M 16/00* (2006.01)
*A63B 23/18* (2006.01)

(58) Field of Classification Search
USPC .................................................. 446/200, 202
See application file for complete search history.

(56) References Cited

U.S. PATENT DOCUMENTS

| | | | | | |
|---|---|---|---|---|---|
| 2,282,056 | A | * | 5/1942 | Hoeflich | A63H 5/00 446/209 |
| 2,851,270 | A | * | 9/1958 | Ball | A63H 5/00 124/62 |
| 3,321,976 | A | * | 5/1967 | Jones | A61B 5/097 600/543 |
| 3,559,330 | A | * | 2/1971 | Matlack | A63H 33/40 446/186 |
| 3,863,914 | A | * | 2/1975 | O'Connor | A63B 23/18 482/13 |
| 4,395,933 | A | * | 8/1983 | Shepley | G10D 9/026 84/399 |
| 4,447,250 | A | * | 5/1984 | Woleans | A63H 37/00 2/209.13 |
| 4,579,826 | A | * | 4/1986 | Bolton | A61B 5/082 422/85 |
| 5,110,316 | A | * | 5/1992 | Shaw | G09F 21/02 40/439 |
| D441,033 | S | * | 4/2001 | Li | D21/405 |
| 2009/0156087 | A1 | * | 6/2009 | Lee | A63H 37/00 446/202 |
| 2011/0070804 | A1 | * | 3/2011 | Lee | A63H 5/00 446/202 |

\* cited by examiner

BLOWOUT

CROSS-REFERENCED TO RELATED APPLICATION

This application is a National Phase entry of International Application PCT/JP2014/077778, filed Oct. 20, 2014, which claims priority to Japanese patent application JP2014-178704 filed Sep. 3, 2014, the disclosure of each of which is hereby incorporated in its entirety by reference.

TECHNICAL FIELD

The present invention relates to a blowout (party horn), particularly, a blowout utilizable for health promotion, medical treatment, cosmetic treatment and the like.

BACKGROUND ART

A blowout has been widely known as a "fukimodoshi" toy since a long time ago, which includes a stretchable body (pouch-like portion) having a tube shape, and a wire spring arranged along the longitudinal directions of the stretchable body. If air is blown into the stretchable body from an end thereof, the stretchable body is stretched, while the stretchable body is curled into a spiral by the elastic force of the wire spring when air is not blown into it.

Conventionally, the blowout is mainly used as a toy for children, but a blowout utilizable for health promotion, medical treatment, cosmetic treatment and the like is also known (e.g., refer to Patent Document 1). This type of blowout has a mouthpiece arranged at the air-blowing part thereof, the mouthpiece being formed of an antibacterial, flexible material and being attachable to and detachable from the blowout, so that the blowout can be kept hygienic even if it is repeatedly used over a long period of time.

PRIOR ART DOCUMENTS

Patent Documents

Patent Document 1: Registered Utility Model Publication No. 3137944

SUMMARY OF THE INVENTION

Problems to be Solved by the Invention

A blowout is blown to stretch a stretchable body thereof, and this blowing force (required exhaling force) depends mainly on the elastic force of a spring of the blowout. Conventionally, the required exhaling force (elastic force) is essentially set such that a child as the main user can stretch the stretchable body easily. However, the inventor(s) of the present invention conceive(s) that the required exhaling force for stretching the stretchable body may be desirably variable with the purposes such as health promotion, medical treatment and cosmetic treatment, the user conditions such as the oral function condition and the physical condition of a user, or the like. For example, a required exhaling force suitable for health promotion differs from a required exhaling force suitable for cosmetic treatment, and hence, it is desirable to set a required exhaling force in accordance with the purposes, the user conditions or the like.

The required exhaling force for stretching the stretchable body can be varied by changing the elastic force of the spring. However, the required exhaling force needs to be finely varied with the purposes or the like, and it is difficult to finely adjust the required exhaling force to a specified required exhaling force only by changing the elastic force of the spring. Further, the elastic force of the spring can be unequal to the force necessary for stretching the stretchable body. Consequently, the required exhaling force is difficult to set precisely to a suitable value for a purpose, a user condition or the like.

Therefore, it is an object of the present invention to provide a blowout in which the required exhaling force for stretching a stretchable body thereof can be precisely set to a suitable value for a purpose, a user condition or the like.

Means for Solving the Problems

In order to solve the problems, a blowout according to claim 1 includes: a stretchable body having a tube shape and changeable in shape; a wire body having elasticity and arranged along the longitudinal directions of the stretchable body; a pipe body having a cylinder shape and connected to an end part of the stretchable body; and a mouthpiece body having a cylinder shape and connected to the end part of the pipe body on the opposite side to the stretchable body, the mouthpiece body being held by a user in the mouth such that air is blown by the user, in which the stretchable body is stretched by blowing air from the mouthpiece body while the stretchable body is curled into a spiral by the elastic force of the wire body when air is not blown from the mouthpiece body, wherein: the elastic force of the wire body is set to a predetermined value; the mouthpiece body includes a flow-rate regulating means for regulating the quantity of air flowing toward the stretchable body; and the stretchable body is not stretched unless the force (required exhaling force/exhaled air pressure) by which air is blown from the mouthpiece body is equal or more than a predetermined value.

According to claim 2, in the blowout of claim 1, the flow-rate regulating means includes a restricting portion united with the mouthpiece body and restricting the flow rate of air, and a restricting body having a ring shape, attached to the mouthpiece body and restricting the flow rate of air.

According to claim 3, in the blowout of claim 1 or 2: the stretchable body is formed by a first material having a substantially quadrilateral sheet shape and a second material having a long strip shape; the first material is shaped into a tube by placing one end part of the first material on top of the other end part of the first material; the wire body is arranged on the external surface of an overlap part between the one end part and the other end part; and the second material is joined to the first material such that the second material covers the external surface of the overlap part, so that the wire body is united to the stretchable body.

According to claim 4, in the blowout of claims 1 to 3, a plurality of the wire bodies are provided, and the stretchable body is not stretched unless the force by which air is blown from the mouthpiece body is equal or more than a predetermined value.

Advantages of the Invention

In the blowout of claim 1, the elastic force of the wire body is set to a predetermined value, and further, the mouthpiece body includes a flow-rate regulating means for regulating the quantity of air flowing toward the stretchable body. Therefore, the stretchable body will not be stretched unless the force by which air is blown from the mouthpiece body is equal or more than a predetermined value. In other words, both the elastic force of the wire body and the regulation of the quantity of air by the flow-rate regulating means determine the required exhaling force for stretching the stretchable body. Hence, both the wire body and the flow-rate regulating means are adjusted, so that the required exhaling force can be precisely set to a suitable value for a purpose, a user condition or the like.

In the blowout of claim 2, the flow-rate regulating means includes the restricting portion and the restricting body. Therefore, both the restricting portion and the restricting body are adjusted, so that the quantity of air flowing toward the stretchable body can be finely regulated more precisely. Accordingly, the required exhaling force for stretching the stretchable body can be more precisely set to a suitable value for a purpose, a user condition or the like.

In the blowout of claim 3, the wire body is united to the stretchable body, and thereby, the elastic force of the wire body is directly transmitted to the stretchable body. This means that the elastic force set for the wire body directly affects the required exhaling force for stretching the stretchable body. Accordingly, the required exhaling force can be more precisely set to a specified suitable value simply by setting the elastic force of the wire body to a predetermined value. Further, the wire body is arranged on the overlap part between the one end part and the other end part of the first material, and the second material is arranged on the wire body. Therefore, the wire body is strongly held between the two materials and thereby is securely united to the stretchable body.

In the blowout of claim 4, a plurality of the wire bodies are provided, and the wire bodies determine the required exhaling force for stretching the stretchable body. Accordingly, the number of the wire bodies is adjusted, so that the required exhaling force can be more precisely set to a specified suitable value.

MODE FOR CARRYING OUT THE INVENTION

An embodiment of the present invention will be below described with reference to the drawings.

Figure 1:
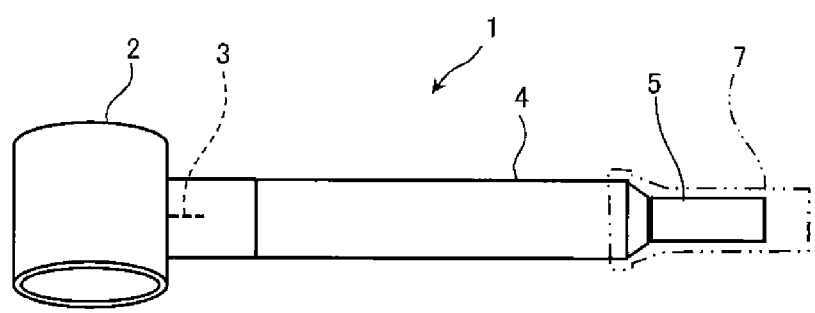
FIG. 1 is a perspective view of a blowout according to an embodiment of the present invention.

FIGS. 1 to 4 show an embodiment of the present invention, and FIG. 1 is a perspective view of a blowout 1 according to this embodiment. The blowout 1 is particularly utilizable for health promotion, medical treatment, cosmetic treatment and the like, and mainly includes a stretchable body 2, a wire body 3, a pipe body 4, a mouthpiece body 5 and an air regulating body (flow-rate regulating means) 6.

Figure 2:
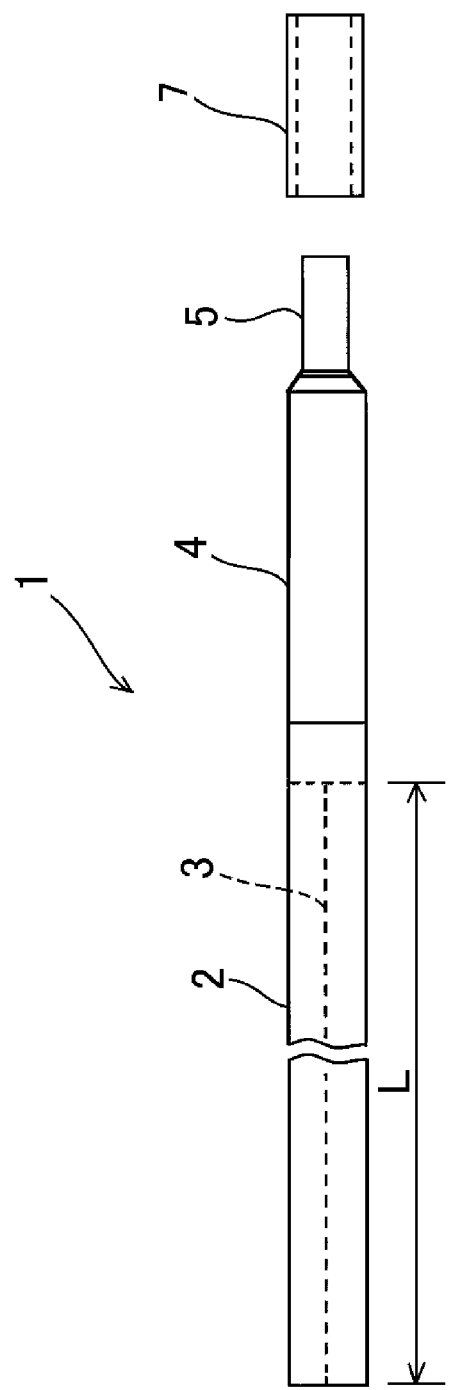
FIG. 2 is a plan view showing a stretchable body of the blowout of FIG. 1 being stretched.

The stretchable body 2 is a pouch-like portion having a tube shape and changeable in shape, and is formed by sheets of paper 21 and 22 having predetermined material qualities (properties) such as thickness, strength, density (weight per unit area) and durability. As shown in FIG. 2, the stretchable body 2 has a ring shape in cross section when inflated with air blown into the stretchable body 2. The inner diameter thereof is designed to be slightly larger than the outer diameter of the pipe body 4. The stretchable body 2 is shaped into a tube by bending a first material having a substantially rectangular (substantially quadrilateral) sheet shape (described later).

A length L of the stretchable body 2 (except the insertion part of the pipe body 4 into the stretchable body 2) is set in accordance with the purposes (what the blowout 1 is used for) such as health promotion, medical treatment and cosmetic treatment, the user conditions such as the oral function condition and the physical condition of a user, or the like. Specifically, the length L of the stretchable body 2 is set such that the quantity of air necessary for stretching out the stretchable body 2 over the full length L equates with a suitable quantity of air preset for a purpose, a user condition or the like.

The wire body 3 is a wire having elasticity and arranged straight along the longitudinal directions of the stretchable body 2. Specifically, the wire body 3 is formed of stainless-steel wire and is curled into a spiral/coil when not given an external force (when air is not blown into the stretchable body 2). If the wire body 3 is released after straightened by an external force, the wire body 3 returns to the spiral shape by an elastic force of its own. The elastic force (elastic modulus) is set to a predetermined value such that the required exhaling force for stretching the stretchable body 2 becomes a suitable value set in accordance with the purposes, the user conditions or the like, in other words, such that the stretchable body 2 will be not stretched unless the force (exhaled air pressure) by which air is blown from the mouthpiece body 5 is equal or more than the suitable value (predetermined value).

As the suitable value, for example, for the purpose of health promotion, different suitable values, in order from low, level 0, level 1 and level 2 can beset in accordance with the oral function condition, physical condition (age) or the like of a user. In short, suitable values for the blowing force (exhaled air pressure) are finely set in accordance with the purposes, the user conditions or the like.

Further, a plurality of the wire bodies 3 may be provided when the single wire body 3 cannot precisely offer the elastic force equivalent to a predetermined value, or when a plurality of the wire bodies 3 can more precisely and easily offer the elastic force equivalent to a predetermined value. The plurality of wire bodies 3 could make it possible that the stretchable body 2 will be not stretched unless the force by which air is blown from the mouthpiece body 5 is equal or more than a suitable value (predetermined value). For example, the one wire body 3 offering the elastic force of a predetermined value is provided for the level 1, and the two wire bodies 3 each offering the elastic force of the same predetermined value are provided for the level 2.

Figure 3:
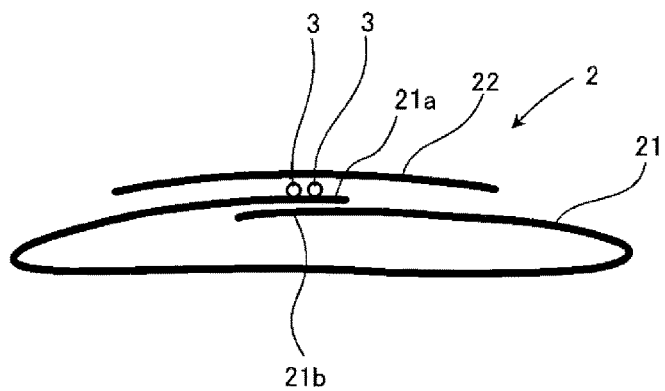
FIG. 3 is a cross-sectional view showing how to arrange wire bodies of the blowout of FIG. 1.

The wire body 3 is, as shown in FIG. 3, housed in the stretchable body 2 such that it is located inside of each ring of the spiral of the stretchable body 2. Specifically, the stretchable body 2 is formed by the substantially rectangular first material 21 and the long-strip shaped second material 22. The first material 21 is shaped into a tube by placing one end part 21a of the first material 21 on top of the other end part 21b of the first material 21 and gluing the one end part 21a to the other end part 21b. Then, the wire body 3 is arranged on the external surface (outer surface) of an overlap part 21c between the one end part 21a and the other end part 21b. In this state, the second material 22 is glued/joined to the first material 21 such that the second material 22 covers the whole external surface of the overlap part 21c. Thereby, the wire body 3 is united to the stretchable body 2.

As described above, the wire body 3 is arranged on the overlap part 21c between the one end part 21a and the other end part 21b of the first material 21, and further, the second material 22 is arranged on the wire body 3. Therefore, the wire body 3 is strongly held between the two materials 21 and 22, and thereby, is securely united to the stretchable body 2. FIG. 3 shows that the two wire bodies 3 are provided, and the number of the wire bodies 3 is set as previously described.

The pipe body 4 is a pipe portion having a cylinder shape and connected to an end part of the stretchable body 2. Specifically, the pipe body 4 is a cylinder formed by a sheet of paper having a specified quality of material, and as shown in FIG. 2, one end part thereof is inserted into the end part of the stretchable body 2 and connected thereto with vinyl tape or the like. The pipe body 4 has such an inner diameter and a length that a user can hold it easily and blow air easily from the mouthpiece body 5 into the stretchable body 2.

The mouthpiece body 5 is a mouthpiece portion having a cylinder shape and connected to the end part (the other end part) of the pipe body 4 on the opposite side to the stretchable body 2. A user holds the mouthpiece body 5 in the mouth and blows air in. The mouthpiece body 5 is provided inside with the air regulating body 6 for regulating the quantity of air flowing toward the stretchable body 2.

Figure 4:
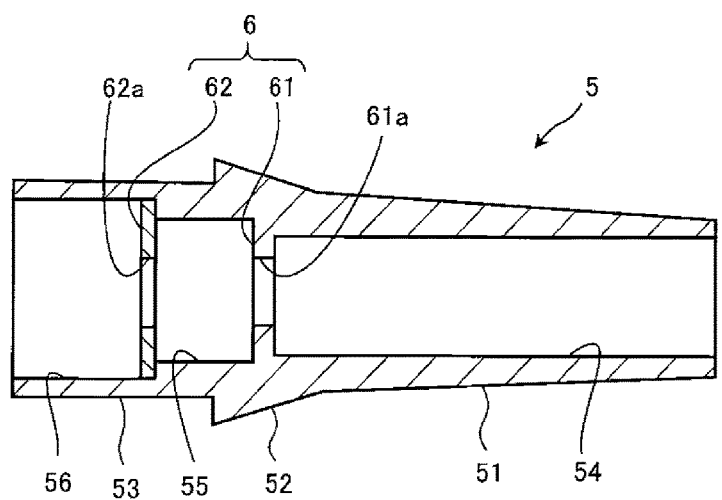
FIG. 4 is a longitudinal sectional view of a mouthpiece body of the blowout of FIG. 1.

The mouthpiece body 5 is made of resin, and as shown in FIG. 4, includes a first barrel portion 51, a second barrel portion 52 and a third barrel portion 53. The first barrel portion 51 has a cylinder shape slightly tapering to an end thereof. The second barrel portion 52 is arranged at the other end of the first barrel portion 51 and has a cone shape small in outer diameter on the side of the first barrel portion 51. The third barrel portion 53 is arranged at the end of the second barrel portion 52 on the opposite side to the first barrel portion 51, and has an outer diameter substantially equal to the inner diameter of the pipe body 4. The third barrel portion 53 is inserted/pressed into the pipe body 4, and thereby, the mouthpiece body 5 is connected to the pipe body 4.

The mouthpiece body 5 is formed inside with: a first hole portion 54 located in the first barrel portion 51 and the second barrel portion 52; a second hole portion 55 located in the second barrel portion 52 and the third barrel portion 53; and a third hole portion 56 located in the third barrel portion 53. The hole portions 54-56 are concentric with the mouthpiece body 5 and have an inner diameter different from each other. The inner diameter becomes larger in the order of the first hole portion 54, the second hole portion 55 and the third hole portion 56 so that air easily flows toward the stretchable body 2.

The air regulating body 6 includes a restricting portion 61 united with the mouthpiece body 5 and restricting the flow rate of air, and a restricting body 62 having a ring shape, attached to the mouthpiece body 5 and restricting the flow rate of air. The restricting portion 61 is a partition wall between the first hole portion 54 and the second hole portion 55, and is formed at the center with a first restriction hole 61a. From the first hole portion 54, air flows through the first restriction hole 61a and thereby the flow rate of the air is restricted, so that the air can be sent at a predetermined flow rate to the second hole portion 55.

The restricting body 62 is a metal disk having an outer diameter substantially equal to the inner diameter of the third hole portion 56, and is inserted/pressed into the third hole portion 56 and attached to the step part between the second hole portion 55 and the third hole portion 56. The restricting body 62 is formed at the center with a second restriction hole 62a. From the second hole portion 55, air flows through the second restriction hole 62a and thereby the flow rate of the air is restricted, so that the air is sent at a predetermined flow rate to the third hole portion 56. In this embodiment, the first restriction hole 61a and the second restriction hole 62a each have a diameter which is substantially half the diameter of the first hole portion 54.

As described above, the restricting portion 61 and the restricting body 62 restrict the flow rate of air blown into them and send the air to the stretchable body 2. Therefore, the stretchable body 2 will not be stretched unless the force by which air is blown from the mouthpiece body 5 is equal or more than a predetermined value. In other words, the flow-rate restrictions (the diameters of the restriction holes 61a and 62a) of the restricting portion 61 and the restricting body 62 are set such that the stretchable body 2 will not be stretched unless the force (exhaled air pressure) by which air is blown from the mouthpiece body 5 is equal or more than a suitable value set in accordance with the purposes, the user conditions or the like.

In consideration of the quality of material, inner diameter, length and the like of the stretchable body 2 and the pipe body 4, therefore, an elastic force (elastic modulus) of the wire body 3, the number of wire bodies 3 and a flow-rate restriction (regulated air quantity) by the air regulating body 6 are set such that the required exhaling force for stretching a stretchable body 2 becomes a suitable value set in accordance with the purposes, the user conditions or the like. In other words, the elastic force of the wire body 3 or the flow-rate restriction by the air regulating body 6 is adjusted such that the stretchable body 2 will not be stretched unless the force (exhaled air pressure) by which air is blown from the mouthpiece body 5 is equal or more than a suitable value (predetermined value).

The mouthpiece body 5 is provided with a mouthpiece 7 attachable thereto. The mouthpiece 7 is formed of a flexible material (e.g., silicone) subjected to antibacterial treatment. As shown in FIGS. 1 and 2, the mouthpiece 7 is a semi-transparent cylinder, and into the cylinder, the mouthpiece body 5 is inserted and then the pipe body 4 is pressed so that the mouthpiece 7 can be attached to the mouthpiece body 5. The mouthpiece 7 enables a user to hold the mouthpiece body 5 comfortably in the mouth and keeps the mouthpiece body 5 hygienic even if repeatedly used over a long period of time.

In the thus configured blowout 1, a user blows air from the mouthpiece body 5 (the mouthpiece 7), and thereby, as shown in FIG. 2, the air is sent into the stretchable body 2 to stretch the stretchable body 2. On the other hand, when air is not blown from the mouthpiece body, as shown in FIG. 1, the stretchable body 2 is curled into a spiral again by the elastic force of the wire body 3. In this process, the stretchable body 2 will not continue stretching unless the force (exhaled air pressure) by which air is blown from the mouthpiece body 5 is equal or more than a suitable value (predetermined value) set in accordance with the purposes, the user conditions or the like. Unless the quantity of air blown from the mouthpiece body 5 does not reach a preset quantity of air in accordance with the purposes, the user conditions or the like, the stretchable body 2 will not stretch out over the full length L. Therefore, a user utilizes the blowout 1 and stretches (blows out) the stretchable body 2 repeatedly, and thereby, the user can exercise and train by a blowing force suitable for a purpose, a user condition or the like.

As described above, in the blowout 1, the elastic force of the wire body 3 is set to a predetermined value, and further, the air regulating body 6 is provided for regulating the quantity of air flowing toward the stretchable body 2.

Therefore, the stretchable body 2 will not be stretched unless the force (exhaled air pressure) by which air is blown from the mouthpiece body 5 is equal or more than a predetermined value. In other words, the required exhaling force (required exhaled-air pressure) for stretching the stretchable body 2 is set by utilizing both the elastic force of the wire body 3 and the regulation of the quantity of air (restrictions on the flow rate of air) by the air regulating body 6.

Accordingly, both the wire body 3 and the air regulating body 6 are adjusted, so that the required exhaling force can be precisely set to a suitable value for a purpose, a user condition or the like. Specifically, even if suitable values for the blowing force (exhaled air pressure) are finely set in accordance with the purposes such as health promotion, medical treatment and cosmetic treatment, the user conditions such as the oral function condition and the physical condition of a user, or the like, then the required exhaling force can be precisely set to the respective suitable values.

Further, the air regulating body 6 includes the restricting portion 61 and the restricting body 62. Therefore, the flow-rate restrictions of both the restricting portion 61 and the restricting body 62 are adjusted, so that the quantity of air flowing toward the stretchable body 2 can be finely regulated more precisely. Accordingly, the required exhaling force for stretching the stretchable body 2 can be more precisely set to a suitable value for a purpose, a user condition or the like. Still further, the restricting body 62 is a separate body from the mouthpiece body 5, and hence, the restricting bodies 62 each formed with the second restriction holes 62*a* having different diameters can be attached to the mouthpiece body 5. Thereby, the flow-rate restriction (regulated air quantity) by the air regulating body 6 can be adjusted and varied easily without exchanging the mouthpiece body 5 for another.

In addition, the wire body 3 is strongly held between the two materials 21 and 22 and is securely united to the stretchable body 2, and thereby, the elastic force of the wire body 3 is directly transmitted to the stretchable body 2. This means that the elastic force set for the wire body 3 directly affects the required exhaling force for stretching the stretchable body 2. Accordingly, the required exhaling force can be more precisely set to a specified suitable value simply by setting the elastic force of the wire body 3 to a predetermined value.

If the wire body 3 is merely arranged along the stretchable body 2 and glued thereto, then the wire body 3 becomes a separate body from the stretchable body 2, thereby hindering the elastic force of the wire body 3 from being directly transmitted to the stretchable body 2. This means that the elastic force (recoiling force) of the stretchable body 2 differs from the elastic force of the wire body 3, thereby affecting and varying the required exhaling force for stretching the stretchable body 2. In contrast, the blowout 1 does not undergo the influence and variation because the wire body 3 is securely united to the stretchable body 2. Accordingly, the required exhaling force can be more precisely set to a specified suitable value.

Furthermore, the plurality of wire bodies 3 are provided, and the wire bodies adjust and determine the required exhaling force for stretching the stretchable body. Accordingly, the required exhaling force can be more precisely set to a specified suitable value.

Although the embodiment of the present invention has been above described, the present invention is not limited to the embodiment as a specific configuration thereof. Without departing from the scope of the present invention, variations or the like in design should be included in the present invention. For example, in the above embodiment, the one pipe body 4 is provided with the single stretchable body 2. However, in accordance with the usage purposes of the blowout 1, the conditions of a user or the like, the one pipe body 4 may be provided with a plurality of the stretchable bodies 2. Further, the stretchable body 2 may have a scale so that a user can visually check easily how much the stretchable body 2 is stretched.

DESCRIPTION OF THE SYMBOLS

1 blowout
2 stretchable body
21 first material
21*a* one end part
21*b* the other end part
21*c* overlap part
22 second material
3 wire body
4 pipe body
5 mouthpiece body
6 air regulating body (flow-rate regulating means)
61 restricting portion
61*a* first restriction hole
62 restricting body
62*a* second restriction hole
7 mouthpiece

The invention claimed is:

1. A blowout including: a stretchable body having a tube shape and changeable in shape; a wire body having elasticity and arranged along the longitudinal direction of the stretchable body; a pipe body having a cylinder shape and connected to an end part of the stretchable body, wherein the pipe body has an internal opening in fluid communication with the stretchable body; and a mouthpiece body having a cylinder shape and connected to the end part of the pipe body on the opposite side of the stretchable body wherein the mouthpiece body has a first hole portion and an internal opening in fluid communication with the first hole portion, the internal opening having a diameter; wherein the stretchable body is stretched when air is blown by the user into the first hole opening, and the stretchable body is curled into a spiral by the elastic force of the wire body when air is not blown into the first hole opening, wherein:

the elastic force of the wire body is set to a predetermined value;

the mouthpiece body includes a flow-rate regulating section for regulating the quantity of air flowing toward the stretchable body, wherein the flow regulating section comprises;

at least one removable and replaceable restricting body, having at least a first restricting hole in fluid communication with the first hole opening, wherein the first restricting hole has a diameter less than the internal diameter of the mouthpiece body, wherein;

the stretchable body is not stretched unless the force by which air is blown into the first hole portion is equal or more than a predetermined value, and the predetermined value is at least partially defined by the wire body elastic force value and the diameter of the first restricting hole in the installed restricting body.

2. The blowout according to claim 1, wherein the flow-rate regulating section further includes a restricting portion united with the mouthpiece body having at least a second hole opening for restricting the flow rate of air, wherein the second restricting hole has a diameter less than the internal diameter of the mouthpiece body.

3. The blowout according to claim 2, wherein the first hole portion has a first diameter, the second restricting hole has a diameter which is substantially half of the diameter of the first hole portion.

4. The blowout according to claim 1, wherein: the stretchable body is formed by a first material having a substantially quadrilateral sheet shape and a second material having a long strip shape;

the first material is shaped into a tube by placing one end part of the first material on top of the other end part of the first material; the wire body is arranged on the external surface of an overlap part between the one end part and the other end part; and the second material is joined to the first material such that the second material covers the external surface of the overlap part, so that the wire body is united to the stretchable body.

5. The blowout according to claim 1, wherein a plurality of the wire bodies are provided, and the stretchable body is not stretched unless the force by which air is blown from into the first hole opening is equal or more than a predetermined value.

6. The blowout according to claim 1, wherein the mouthpiece body further includes a replaceable mouthpiece which at least partially surrounds the mouthpiece body.

7. The blowout according to claim 1, wherein the mouthpiece comprises silicone.

8. The blowout according to claim 1, wherein the first hole portion has a first diameter and the first restricting hole has a diameter which is substantially half of the diameter of the first hole portion.

9. The blowout according to claim 8, wherein the flow-rate regulating section further includes a restricting portion united with the mouthpiece body having at least a second hole opening for restricting the flow rate of air, wherein the second restricting hole has a diameter which is substantially half of the diameter of the first hole portion.

* * * * *